United States Patent [19]

Takenaka et al.

[11] 4,246,107
[45] Jan. 20, 1981

[54] SEPARATION OF LYMPHOCYTES FROM LYMPHOCYTE-CONTAINING SUSPENSION BY FILTRATION

[75] Inventors: Yoshinori Takenaka; Nobuaki Tsuda; Toru Kuroda, all of Fuji, Japan

[73] Assignee: Asahi Kasei Kogyo Kabushiki Kaisha, Osaka, Japan

[21] Appl. No.: 16,600

[22] Filed: Mar. 1, 1979

[30] Foreign Application Priority Data

Mar. 6, 1978 [JP] Japan .................................. 53-24476
Mar. 6, 1978 [JP] Japan .................................. 53-24477
Jul. 21, 1978 [JP] Japan .................................. 53-88339
Nov. 10, 1978 [JP] Japan ................................ 53-137849

[51] Int. Cl.³ ............................................ B01D 25/06
[52] U.S. Cl. .................................. 210/806; 210/259; 210/317; 210/927
[58] Field of Search ............... 210/65, 73 R, 314, 316, 210/317, 333, 335, 435, 446, 483, 491, DIG. 23, 259; 128/214 R

[56] References Cited

U.S. PATENT DOCUMENTS

| 2,302,552 | 11/1942 | Johnson | 210/317 |
|---|---|---|---|
| 3,448,041 | 6/1969 | Swank | 210/316 |
| 3,954,621 | 5/1976 | Etani et al. | 210/314 |
| 4,073,723 | 2/1978 | Swank et al. | 210/DIG. 23 |
| 4,116,845 | 9/1978 | Swank | 210/DIG. 23 |

FOREIGN PATENT DOCUMENTS 877475 8/1971 Canada ........................... 210/DIG. 23

Primary Examiner—Ivars C. Cintins
Attorney, Agent, or Firm—Sprung, Felfe, Horn, Lynch & Kramer

[57] ABSTRACT

Lymphocytes are advantageously separated from blood or other lymphocyte-containing suspensions by a method wherein the lymphocyte-containing suspension is flowed through a second filter having a mass of fibers exhibiting an average fiber diameter of greater than 10 microns but not greater than 60 microns, thereby to entrap a substantial part of granulocytes and monocytes in the mass of fibers and to obtain a granulocyte-poor and monocyte-poor lymphocyte-containing suspension; and then, the obtained suspension is flowed through a first filter having a mass of fibers exhibiting a bulk density of 0.04 to 0.40 g/cm³ and an average fiber diameter of 5 to 20 microns, said average fiber diameter being less than that of the second filter, thereby to entrap a substantial part of lymphocytes in the mass of fibers; and finally, the lymphocytes entrapped in the mass of fibers of the first filter is collected.

Alternatively, another method is employed wherein the lymphocyte-containing suspension is flowed through the first filter thereby to entrap a substantial part of leukocyte components therein; and the leukocyte components entrapped in the first filter is collected to obtain a leukocyte component-rich suspension; and finally, the leukocyte component-rich suspension is flowed through the second filter thereby to entrap a substantial part of granulocytes and monocytes in the second filter and to obtain a lymphocyte-rich suspension.

12 Claims, 10 Drawing Figures

SEPARATION OF LYMPHOCYTES FROM LYMPHOCYTE-CONTAINING SUSPENSION BY FILTRATION

BACKGROUND OF THE INVENTION

This invention relates to a method of and an apparatus for separating lymphocytes from a lymphocyte-containing suspension by filtration.

By the term "lymphocyte-containing suspension" used herein is meant blood, ascites, bone marrow and other lymphocyte- or lymphocyte precursor cell-containing body fluids. This term should also be interpreted as including physically, chemically and/or biologically treated blood and other body fluids such as, for example, blood diluted with a physiological solution, erythrocyte agglutinant-(such as dextran or hydroxyethylstarch)-incorporated blood, a buffy coat and other lymphocyte-containing suspension layers prepared by centifugation or cell-electrophoresis.

In recent years lymphocytes collected from blood have been in frequent use in the field of immunology. For example, lymphocytes are used for immunological studies directed to histocompatibility antigens and cellular immunity. Lymphocytes are also used for determining lymphocyte blastotransformation or for determining the proportion of T-cells to B cells, and for trying to separate helper T-cells and suppressor T cells from T cells. Furthermore, lymphocyte component transfusions have been studied in great detail.

Various processes have been employed for carrying out lymphocyte separation. Typical separation processes include, for example, a density gradient centrifugation process such as the Ficoll-Conray process, an anticoagulant incorporation-sedimentation-(or centrifugation)-adhering process and a cell electrophoresis process.

The centrifugation process involves, for example, placing a plurality of liquids of different densities, one upon another, in a vessel to form density gradient superposed layers; placing blood on the top liquid layer; and then centrifuging the superposed layers thereby to separate the blood into several layers.

The anticoagulant incorporation-sedimentation-(or centrifugation)-adhering process involves incorporating an anticoagulant into a lymphocyte-containing suspension, subjecting the anticoagulant-incorporated suspension to sedimentation or centrifugation to separate the suspension into an erythrocyte sediment and a leukocyte-containing liquid layer, then introducing the leukocyte-containing liquid layer into a column having packed therein a mass of fibers such as glass wool, cotton or nylon wool, wherein the liquid is maintained at a temperature of 37° C. for a period of approximately 30 minutes to entrap granulocytes and monocytes in the mass of fibers, and finally collecting lymphocytes.

The above-mentioned conventional processes have several disadvantages as will now be described. The density gradient centrifugation process requires a substantial period of time and skill to carry out the centrifugation step completely. When this process is employed, lymphocytes are likely to be undesirably changed during such a long period of time and, furthermore, to be damaged by the centrifugation and repeated washing operations. The density gradient centrifugation process further requires the use of a plurality of expensive apparatuses. When the lymphocytes collected by this centrifugation process are used for transfusion, additives such as a Ficoll-Conray solution or gum arabic are required to be removed from the collected lymphocytes.

In the anticoagulant incorporation-sedimentation-adhering process, a substantial period of time is required to complete separation of lymphocytes from the lymphocyte-containing suspension and it is also difficult to collect a lymphocyte-rich suspension with a high yield. The cell electrophoresis process requires the use of an expensive apparatus and is therefore disadvantageous.

SUMMARY OF THE INVENTION

It is the main object of the present invention to provide a method of and an apparatus for separating lymphocytes from a lymphocyte-containing suspension, which filter unit insures an effective filtration of a lymphocyte-containing suspension and an effective collection of lymphocytes with enhanced yield and purity and within a reasonably short period of time.

Other objects and advantages of the present invention will become apparent from the following description.

In one aspect of the present invention there is provided an apparatus for separating lymphocytes from blood or other lymphocyte-containing suspensions, comprising:

a first filter comprising a container having packed therein a mass of fibers exhibiting a bulk density of from 0.04 to 0.40 gram/cubic centimeter and an average fiber diameter of from 5 to 20 microns, and a second filter disposed upstream to or downstream from the first filter, comprising a container having packed therein a mass of fibers exhibiting an average fiber diameter of greater than 10 microns but not greater than 60 microns, the average fiber diameter of the second filter being greater than that of the first filter, an outlet of one of the two filters being connected to an inlet of the other filter.

In another aspect of the present invention, there is provided a method of separating lymphocytes from a lymphocyte-containing suspension comprising the steps of:

causing the lymphocyte-containing suspension to flow through a second filter comprising a container having packed therein a mass of fibers exhibiting an average fiber diameter of greater than 10 microns but not greater than 60 microns, thereby to entrap a substantial part of the granulocytes and monocytes in the mass of fibers and to obtain a granulocyte-poor and monocyte-poor lymphocyte-containing suspension, causing the granulocyte-poor and monocyte-poor lymphocyte-containing suspension to flow through a first filter comprising a container having packed therein a mass of fibers exhibiting a bulk density of from 0.04 to 0.40 gram/cubic centimeter and an average fiber diameter of from 5 to 20 microns, the average fiber diameter being less than that of the second filter, thereby to entrap a substantial part of the lymphocytes in the mass of fibers, and then collecting the lymphocytes entrapped in the mass of fibers of the first filter, to obtain a lymphocyte-rich suspension.

In a still further aspect of the present invention there is provided a method of separating lymphocytes from a lymphocyte-containing suspension comprising the steps of:

causing the lymphocyte-containing suspension to flow through a first filter comprising a container having packed therein a mass of fibers exhibiting a bulk density of from 0.04 to 0.40 gram/cubic centimeter and an average fiber diameter of from 5 to 20 microns, thereby to entrap a substantial part of the leukocyte components in the mass of fibers, collecting the leukocyte components entrapped in the mass of fibers of the first filter, to obtain a leukocyte component-rich suspension, and then causing the leukocyte component-rich suspension to flow through a second filter comprising a container having packed therein a mass of fibers exhibiting an average fiber diameter of greater than 10 microns but not greater than 60 microns, the average fiber diameter of the second filter being greater than that of the first filter, thereby to entrap a substantial part of the granulocytes and monocytes in the mass of fibers of the second filter and to obtain a lymphocyte-rich suspension.

BRIEF DESCRIPTION OF THE DRAWINGS

The invention will be more readily understood from the following description, taken in connection with the accompanying drawings, in which.

DESCRIPTION OF THE PREFERRED EMBODIMENTS

Figure 1:
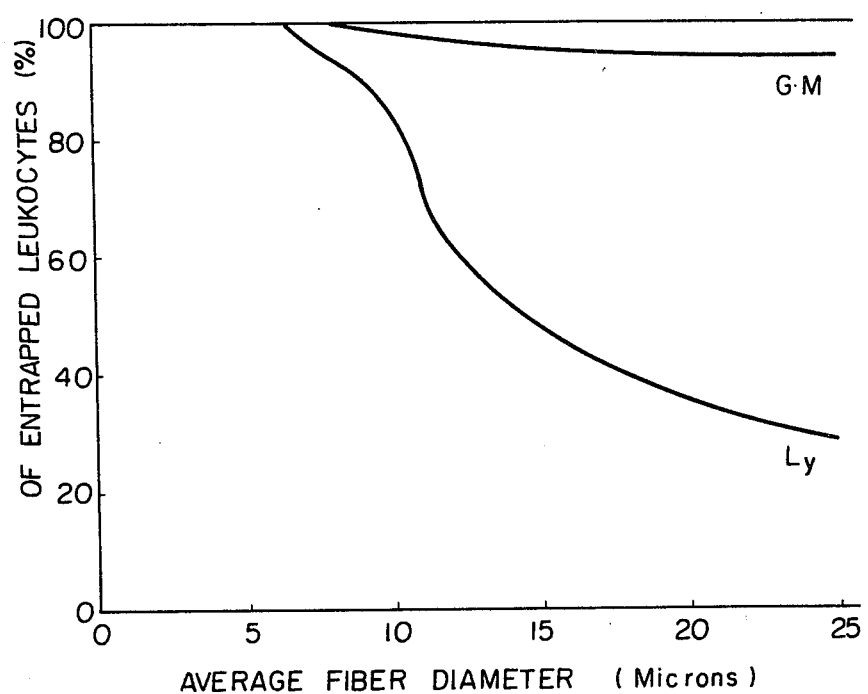
FIG. 1 is a graph showing the dependency of the percentages of entrapped lymphocytes and of granulocytes plus monocytes upon the average fiber diameter as determined at a fiber bulk density of 0.085 gram/cubic centimeter.

Referring now to FIG. 1 which shows the relationship between the average diameter of each of the fibers in the filter and the percentages of leukocyte components, i.e., lymphocytes, granulocytes and monocytes, entrapped by the filter. In FIG. 1, curves Ly and G.M refer to the percentages of lymphocytes and of granulocytes plus monocytes, respectively, entrapped by the filter.

The percentages of the respective leukocyte components are defined by the following equation:

% of entrapped leukocyte
component $= [(A-B)/A] \times 100$ where A is the number of the cells of each leukocyte component in one microliter of the original (i.e., untreated) lymphocyte-containing suspension, and B is the number of the cells of each leukocyte component in one microliter of the suspension passed through the filter.

The term "fiber diameter" used herein is defined by the following equation:

$$D = \sqrt[2]{\frac{x}{\pi \cdot \rho \cdot y}}$$

where D is the diameter of the fiber in centimeters, x is the weight of the fiber in grams, y is the length of the fiber in centimeters, and $\rho$ is the density of the fiber in gram/cubic centimeter. The fibers used are generally of a circular cross-section, but the above-mentioned definition for the fiber diameter should also be applied to fibers of a non-circular cross-section.

The curves G.M and Ly in FIG. 1 were obtained from the following experiments. Polyacrylonitrile fibers having various average diameters were separately packed into a cylindrical polyvinyl chloride column at a bulk density of 0.085 gram/cubic centimeter. The cylindrical polyvinyl chloride column exhibited an inner diameter of 1.0 centimeter and a length of 10 centimeters. Twenty milliliters of blood were pumped into the polyacrylonitrile fiber-packed column, the blood flowed through the column at a flow rate of 2 milliliters/minute, and 12.7 milliliters of blood passed through the filter.

The blood used was heparinized blood of a temperature of 25° C., containing $5.0 \times 10^6$ erythrocytes/microliter, 6,600 leukocytes/microliter (2,300 lymphocytes/microliter and 4,300 granulocytes plus monocytes/microliter) and $2.5 \times 10^5$ platelets/microliter. The above-mentioned experiment was carried out at a temperature of 25° C.

As is apparent from FIG. 1, the smaller the average diameter of the packed fibers, the higher the percentage of lymphocytes entrapped by the packed fibers. Particularly, when the average diameter of the packed fibers is not greater than 10 microns, the percentage of entrapped lymphocytes is satisfactory. The percentage of granulocytes plus monocytes entrapped by the packed fibers is at a high level even when the average fiber diameter is large. From these facts, it will be apparent that the second filter in the apparatus of the invention, which filter is comprised of fibers having a relatively large average diameter, is suitable for selectively entrapping granulocytes and monocytes therein and that the first filter which is comprised of fibers having a relatively small average diameter, is suitable for selectively entrapping therein leukocytes including lymphocytes.

The fibers to be packed in the container of each of the two filters are selected from synthetic fibers, semisynthetic fibers, regenerated fibers, natural fibers such as cotton and silk, and inorganic fibers such as carbon fibers, glass fibers and metal fibers. Each of these mentioned types of fibers may be used by itself or a combination of the different types mentioned may be used. The fibers used should not have any deleterious effects on lymphocytes and other blood components. Accordingly, the fibers should not be made of polymers which have moieties exhibiting, for example, a hemolytic function, and should not be treated with oiling agents which are harmful to blood. Preferable fibers may be selected from synthetic fibers such as acrylonitrile polymer (homopolymer and copolymer) fibers, polyamide fibers and polyester fibers, semi-synthetic fibers such as cellulose acetate fibers, and natural proteinaceous fibers such as silk.

The container in which the mass of fibers is to be packed may be of any shape provided that the container has at least one inlet conduit and at least one outlet conduit through which a lymphocyte-containing suspension and other treated body fluids or physiological solutions can be introduced into and withdrawn from the container, respectively. It is convenient, however, that the container be of a columar shape, i.e., a cylindrical shape or a circular truncated cone shape, in view of ease in operation. It is also convenient that the container be provided, at locations upstream to and downstream from the mass of fibers, with mesh screens or other similar filters in order to prevent the fibers from escaping out of the container. The container may be made of a non-deleterious material such as glass, polyethylene, polypropylene, polystyrene and polyvinyl chloride.

By the term "bulk density" used herein is meant a numerical value expressed in grams/cubic centimeter obtained by dividing the weight (in grams) of the mass of fibers by the volume of the mass of fibers, i.e., the inner volume of the container when the container is completely filled with the mass of fibers.

The mass of fibers packed in the container should preferably have identical bulk densities in any portion of the mass of fibers. It is preferable that the fibers be unbound into single fibers before being packed into the containers. The fibers should also preferably possess a particular length by which the fibers can be kept together in the form of an entangled or interlaced mass. If the fibers are too short, they will tend to escape from the container together with the liquid flowing through the container. For this reason the fibers should preferably possess a length which is at least approximately equal to that of commercially available fibers popularly employed in the textile industry. In particular, fibers of at least 30 centimeters in length cut from continuous filaments are most preferable for use in this case.

The amount of the fibers to be packed is mainly determined by the amount of the particular lymphocyte-containing liquid to be treated and the flow rate thereof. Fibers of different materials and/or of different diameters may be used in combination provided that the average diameter is in the above-mentioned ranges. The mass of fibers should preferably be in the form of a mass of entangled or interlaced fibers, but such mass may be in a woven, non-woven or knitted fabric form.

Figure 2:
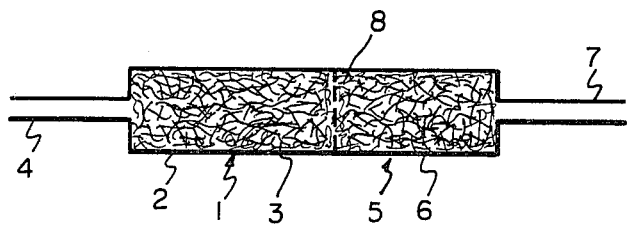
FIG. 2 is a diagrammatic view of one preferred from of the apparatus of the invention.

Referring now to FIG. 2, which shows a preferred embodiment of the apparatus of the invention, the apparatus comprises a second filter 1 for entrapping granulocytes and monocytes therein and a first filter 5 for entrapping leukocytes including lymphocytes therein. The mass of fibers 3 of the second filter 1 and the mass of fibers 6 of the first filter 5 are packed in one and the same container 2, and a mesh screen 8 is provided between the two fiber masses 3 and 6 so that the fibers of one fiber mass are not mixed with the fibers of the other fiber mass. The container 2 has an inlet conduit 4 and an outlet conduit 7.

Figure 3:
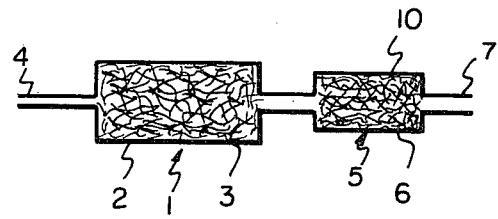
FIG. 3 is a diagrammatic view of another preferred form of the apparatus of the invention.

Referring to FIG. 3, which shows another preferred embodiment of the apparatus of the invention, the mass of fibers 3 of the second filter 1 and the mass of fibers 6 of the first filter 5 are separately packed in two containers 2 and 10, respectively.

Figure 4:
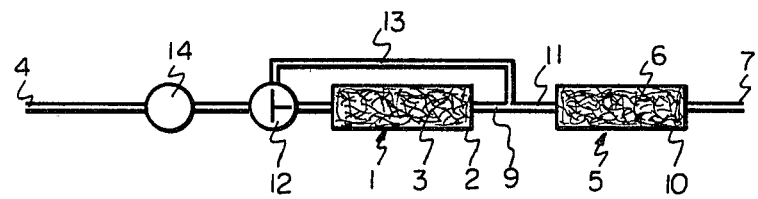
FIG. 4 is a diagrammatic view of a still further preferred form of the apparatus of the invention.

Referring to FIG. 4, which shows still another embodiment of the apparatus of the invention, this apparatus is different from that illustrated with reference to FIG. 3 in that a pump 14 and a three-way cock 12 are provided in the conduit 4. A conduit 13 extends from the three-way cock 12 to the connecting point between a conduit 9 of the second filter 1 and a conduit 11 of the first filter 5. By turning the three-way cock 12, the path of the liquid flow way may be changed so that the suspension is flowed through either the second filter 1 or the conduit 13.

The fibers packed in the container of the first filter should possess an average diameter of from 5 to 20 microns. If the average fiber diameter is too small, a satisfactory number of lymphocytes will be entrapped by the first filter, and it will be difficult to collect the entrapped lymphocytes therefrom. Consequently, the percentage yield of lymphocytes will be low, and it then becomes difficult to obtain a lymphocyte-rich suspension having a particular concentration needed or desired for component transfusions and various medical tests and investigations. In contrast, when the average fiber diameter is too large, the percentage of lymphocytes entrapped by the first filter will be too low, and the percentage yield of lymphocytes will similarly be low.

The fiber bulk density of the first filter should be in the range of from 0.04 to 0.4 gram/cubic centimeter. If the bulk density is too small, the percentage of lymphocytes entrapped by the first filter will be low, leading to a reduction in the concentration of the collected suspension. In contrast, if the bulk density is too large, it then becomes difficult to collect lymphocytes from the first filter. Consequently, the percentage yield of lymphocytes will be low.

The average fiber diameter preferably from 7 to 10 microns, and the fiber bulk density preferably from 0.04 to 0.25 gram/cubic centimeter.

The inner volume of the container of the first filter may usually be varied within the range of from 0.5 to 300 milliliters, depending upon the intended use of the collected lymphocyte-rich suspension.

The collection of the lymphocytes entrpped in the first filter may be conducted by forcing a physiological solution into the first filter. The physiological solution used is not critical and can be, for example, a physiolgical sodium chloride solution, serum, plasma or a mixture thereof.

Figure 9:
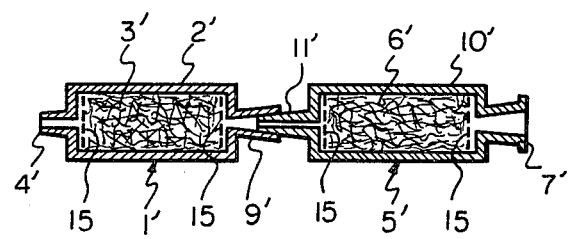
FIG. 9 is a diagrammatic view showing one preferred form of connection for the two filters of the apparatus of the invention.

In the case where the filtration apparatus used is provided with at least one conduit, which is connected to the outlet conduit of one of the two filters and to the inlet conduit of the other filter, as shown in FIG. 4, or in the case where the outlet conduit of one of the two filters can be disconnected from the inlet conduit of the other filter as shown in FIG. 9 hereinafter illustrated, a collecting physiological solution can be forced only into the first filter for collecting the lymphocytes entrapped by the first filter. Accordingly, the granulocytes entrapped by the second filter can be prevented from being disadvantageously incorporated into the collected lymphocyte-rich suspension.

In the case where the filtration apparatus shown in FIG. 4 is used, it is preferable that such forcing of a collecting physiological solution into the first filter be effected while a physical shock is imparted to the filter by, e.g., tapping the periphery of the filter container with a wooden stick, or while the flow rate is maintained at a high level, or while the inner liquid pressure of the filter container is intermittently changed. In the case where the filtration apparatus shown in FIG. 2 or 3 is used, the collecting physiological solution should preferably be forced into the second filter so that the solution flows through the second filter into the first filter at an enhanced flow rate. It is not preferable, in this case, that the collecting physiological solution be allowed to flow while a physical shock is imparted to the filters or that the solution be forced initially into the first filter and thereafter into the second filter. This is because the granulocytes from the second filter are liable to be incorporated into the collected suspension.

The fibers to be packed into the container of the second filter should have an average diameter of greater than 10 microns but of not greater than 60 microns. The average fiber diameter should also be greater than that of the first filter. If the average fiber diameter of the second filter is less than the above-mentioned range, the second filter will entrap a significant amount of lymphocytes as well as granulocytes and monocytes, thus leading to a reduction in the percentage yield of lymphocytes. In contrast, if the average fiber diameter exceeds the above-mentioned range, the percentage of granulocytes and monocytes entrapped by the second filter will decrease, thus reducing the purity of the resultant collected lymphocytes.

The fiber bulk density in the container of the second filter may be suitably varied depending upon the flow rate of the liquid passing therethrough and upon the temperature thereof. The fiber bulk density is preferably in the range of from 0.05 to 0.5 gram/cubic centimeter, more preferably in the range of from 0.1 to 0.4 gram/cubic centimeter.

The inner volume of the container of the second filter may also be varied within a broad range depending upon the intended use of the collected lymphocyte-rich suspension.

Figure 5:
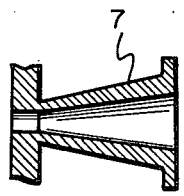
FIG. 5 is a front sectional view of one preferred form of the outlet conduit of the apparatus of the invention.
Figure 6:
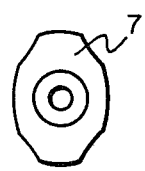
FIG. 6 is a side view of the outlet conduit shown in FIG. 5.

Referring now to FIGS. 5 and 6 which are a front sectional view and a side view, respectively, of one preferred form of the outlet conduit of the filtration apparatus of the invention, the outlet conduit 7 is of a form capable of being connected to an injector by inserting the outlet nipple of an injector into the conduit 7. By the insertion of an injector into the outlet conduit 7, it becomes easy to suck therethrough a lymphocyte-containing suspension or a washing liquor, or to eject therethrough a collecting physiological solution.

Figure 7:
FIGS. 7 and 8 are front sectional views of two preferred forms of the inlet conduit of the apparatus of the invention.
Figure 8:
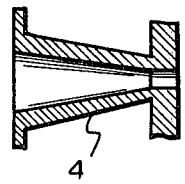

Referring to FIGS. 7 and 8 which are front sectional views of two preferred forms of the inlet conduit of the filtration apparatus of the invention, the inlet conduit 4 is of a form capable of being connected to an injector. That is, the inlet conduit 4 shown in FIG. 7 is of a shape similar to the outlet nipple of an injector, and an injector needle can be fitted to the inlet conduit 4. In place of the form shown in FIG. 7, the inlet conduit 4 may be an injector needle itself. When the inlet conduit 4 is an injector needle, blood can be directly extracted from a donor and sucked into the filtration apparatus. When the inlet conduit is of such a shape that an injector needle can be fitted thereto as shown in FIG. 7, it is possible to extract blood directly from a donor by directly fitting the injector needle to the inlet conduit, and it is also possible to suck blood extracted from a donor through a tube by fitting the tube to the inlet conduit. The inlet conduit 4 shown in FIG. 8 is of a particular shape so as to allow insertion of an outlet nipple of an injector thereinto. After the needle is detached from the injector, the injector which is used for extracting blood can be fitted to the inlet conduit 4 due to its particular shape. By providing the inlet conduit 4 with a rubber cap, the needle of the injector used for extraction of blood can be caused to pierce through the rubber cap.

Referring to FIG. 9 which is a diagrammatic view showing one preferred from of connection for the two filters of the apparatus, the apparatus shown therein is of a relatively small size and is suitable for preparing lymphocyte suspensions for various tests and investigations. The second filter 1' for entrapping granulocytes and monocytes and the first filter 5' for entrapping leukocytes are disposed in a manner similar to that in FIG. 3, except that the two filters are connected to each other by inserting a conduit 11' of the first filter 5' into a conduit 9' of the second filter 1'. Each mass of fibers 3' and 6' is sandwiched by two mesh screens 15 so that the fibers will not escape from the respective containers.

The inner volume of the second filter 1' of the small size filtration apparatus shown in FIG. 9 may be in the range of from 0.5 to 5 milliliters, more preferably from 1 to 3 milliliters. By the term "inner volume of a filter" used herein is meant a volume obtained by subtracting the volume occupied by the fibers from the inner volume of the container. If the inner volume is too small, a substantial period of time is required for the separation of granulocytes and monocytes, or the purity of the resultant collected lymphocytes is reduced. If the inner volume is too large, a large amount of a lymphocyte-containing suspension is needed for obtaining the desired amount of a lymphocyte suspension.

The inner volume of the first filter 5' shown in FIG. 9 may be in the range of from 0.2 to 5 milliliters, more preferably from 0.5 to 3 milliliters. An inner volume which is too small makes it difficult to obtain the desired amount of lymphocyte suspensions and an inner volume which is too large reduces the percentage yield of lymphocytes.

Figure 10:
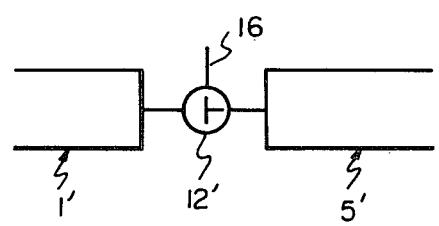
FIG. 10 is a diagrammatic view showing another preferred form of connection for the two filters of the apparatus of the invention.

In the operation of the apparatus shown in FIG. 9, after lymphocytes are entrapped by the first filter 5', the second filter 1' with the granulocytes and monocytes entrapped therein is detached from the first filter 5'. Then, only the first filter 5' is washed, and lymphocytes entrapped by the first filter 5' are collected. Instead of using the arrangement shown in FIG. 9 in which the conduit 9' of the second filter 1' and the conduit 11' of the first filter 5' are detachably connected to each other as shown in FIG. 9, another arrangement as shown in FIG. 10, wherein the two conduits 11' and 9' can be connected to each other by means of a three-way cock 12' which is connected to another conduit 16, can be used. By this three-way cock 12', the washing of only the first filter 5' and the collection of lymphocytes therefrom can be effected.

The method of separating lymphocytes from a lymphocyte-containing suspension by employing the above-explained apparatus will be described.

In the operation of the apparatus shown in FIG. 2 or 3, a lymphocyte-contaning suspension is forced, by using, for example, a pump, through the conduit 4 into the second filter 1. A substantial part of the granulocytes and monocytes present in the original suspension is entrapped by the second filter 1, and the resulting granulocyte-poor and monocyte-poor suspension is forced into the first filter 5 where a substantial part of the lymphocytes is entrapped. Some amounts of erythrocytes, platelets and plasma remain in the first filter 5. In order to obtain the intended lymphocytes of a high purity, these erythrocytes and other components should preferably be washed out from the first filter 5. This washing out may be conducted by introducing into the first filter 5 a physiological solution such as a physiological sodium chloride solution, preferably through the conduit 7 so that the granulocytes entrapped by the second filter 1 can not escape into the first filter. However, if a serum is used as the washing liquor, the serum may be introduced through the conduit 4 although such introduction is not preferable. After the washed liquid is withdrawn from the conduit 4, a physiological solution as a collecting liquid is forced through the conduit 4 into the first filter 5 at an enhanced flow rate, thereby to obtain a lymphocyte-rich suspension with a high purity from the conduit 7. The volume of the collecting liquid may be approximately the same as that of the mass of fibers packed in the first filter 5.

In the operation of the apparatus shown in FIG. 4, a lymphocyte-containing suspension is forced by the pump 14 through the three-way cock 12 into the second filter 1 and then into the first filter 5. After a substantial part of the granulocytes and monocytes is entrapped by the second filter 1 and after a substantial part of the lymphocytes is entrapped by the first filter 5, a physiological solution is forced, through the conduit 4, the three-way cock 12 and the conduit 13, into the first filter 5 thereby to wash out erythrocytes, platelets and plasma remaining in the first filter 5. Thereafter, a collecting physiological solution is similarly forced into the first filter thereby to obtain a lymphocyte-rich suspension.

When a lymphocyte-containing suspension is flowed through the second filter and then the first filter, as explained above, a certain amount of the suspension corresponding to the inner volume of the second filter is not utilized for the separation of lymphocytes. In order to effectively utilize this amount of suspension for the separation of lymphocytes, plasma, serum or a serum-globulin solution may be forced into the second filter whereby the granulocyte-poor and monocyte-poor suspension still including lymphocytes can be flowed from the second filter to the first filter without causing an undesirable desorption of granulocytes and monocytes from the second filter. In the case that the lymphocyte-containing suspension is blood, it is also preferable that a leukocyte-poor suspension passed through the second filter and then the first filter be forced into the second filter again.

In use of the apparatus shown in FIG. 9, the outlet nipple of an injector is first inserted into the conduit 7'; thereafter, a lymphocyte-containing suspension is sucked by the injector through the conduit 4' into the second filter 1' and then into the first filter 5'. After granulocytes and monocytes are entrapped by the second filter and lymphocytes are entrapped by the first filter, the conduit 9' is disconnected from the conduit 11'. Then, a washing physiological solution is sucked by the injector into the first filter. Thereafter, the injector is detached from the conduit 7' of the first filter 5' and, in place of the injector, the outlet nipple of another injector filled with a collecting physiological solution is inserted into the conduit 7'. Finally, the collecting physiological solution is ejected from the injector into the first filter thereby to obtain the intended lymphocyte-rich suspension from the conduit 11'.

Although some preferred embodiments of the invention are described above with reference to the accompanying drawings, modifications may be made thereto. For example, instead of using a pump or injectors as explained above, both a pump and an injector may be used in combination. Or, a lymphocyte-containing suspension and other liquids may be flowed through the two filters by utilizing gravity. Furthermore, instead of utilizing the above-mentioned method wherein a lymphocyte-containing suspension is introduced initially into the second filter and then into the second filter, a modified method can be employed in some cases. For example, first, a lymphocyte-containing suspension is flowed first through only the first filter; thereafter, a washing liquid is flowed through the first filter; next, a collecting liquid is flowed through the first filter to obtain a leukocyte-rich suspension; and finally, the leukocyte-rich suspension is flowed through the second filter thereby to remove granulocytes and monocytes from the suspension and to obtain the intended lymphocyte-rich suspension.

According to the present invention, a lymphocyte-rich suspension can be obtained by using a simple operation and within a relatively short period of time. The obtained suspension contains only very minor amounts of erythrocytes, monocytes and granulocytes, i.e. the purity of the suspension is high. The yield of lymphocytes is also high. Thus, the filtration apparatus of the invention can enable a component transfusion to be easily conducted in medical facilities. It will also be easy to fractionate or adopt a minor amount of lymphocytes required for various medical tests or researches.

The invention will be further illustrated by the following examples carried out at room temperature; in which examples, percentages are shown by the number of cells unless otherwise specified.

EXAMPLE 1

3.817 grams of polyacrylonitrile fibers having an average diameter of 8.2 microns and a length of about 4 centimeters were uniformly packed at a bulk density of 0.15 gram/cubic centimeter into a cylindrical polyvinyl chloride column having an inner diameter of 1.8 centimeters and a length of 10 centimeters, thereby to prepare a first filter. 1.932 grams of polyamide fibers having an average diameter of 20.7 microns and a length of about 4 centimeters were uniformly packed at a bulk density of 0.082 gram/cubic centimeter into another cylindrical polyvinyl chloride column having an inner diameter of 2 centimeters and a length of 7.5 centimeters, thereby to prepare a second filter. The first and second filters were disposed as shown in FIG. 4.

Heparinized blood from a healthy human donor was heated to 37° C., and then caused to flow, by using the pump 14, through the three-way cock 12, the second filter 1 and then the first filter 5, at a flow rate of 4 milliliters/minute. When 100 milliliters of blood were passed through the inlet 4, the pump 14 was stopped and the three-way cock 12 was turned 90° in a clockwise direction. Then, 150 milliliters of a physiological sodium chloride solution were caused to flow, by using the pump 14, through the cock 12, the conduit 13 and then the first filter 5, at a flow rate of 10 milliliters/minute. Finally, 100 milliliters of a collecting liquid of 6.5 pH, comprised of 39.8% of albuminate, 12.5% of an ACD-A solution and 47.7% of a physiological sodium chloride solution, were pumped through the first filter 5 at a flow rate of 10 milliliters/minute, while the periphery of the column 10 was tapped with a wooden stick at a rate of 100 times/minute. The lymphocyte-rich suspension so collected contained 45% of the original lymphocytes and exhibited a viability of at least 99%. The total amount of granulocytes and monocytes contained in the collected lymphocyte-rich suspension was 1% of the total amount of all leukocyte components, that is, the amount of lymphocytes contained in the collected suspension was 99% of the total amount of all leukocyte components (i.e., the purity of lymphocytes was 99%). The collected lymphocyte-rich suspension further contained 1% of the original erythrocytes and 5% of the original platelets.

EXAMPLE 2

1.93 grams of polyamide fibers having an average diameter of 21 microns and a length of about 5 centimeters were uniformly packed at a bulk density of 0.3 gram/cubic centimeter into a cylindrical polyvinyl chloride column having an inner diameter of 15 millimeters and a length of 36 millimeters, thereby to prepare a second filter. The volume of the second filter was 4.7 milliters. 0.263 gram of polyacrylonitrile fibers having an average diameter of 8.16 microns and a length of about 30 millimeters was uniformly packed at a bulk density of 0.131 gram/cubic centimeter into another cylindrical polyvinyl chloride column having an inner diameter of 10 millimeters and a length of 25.5 millimeters, thereby to prepare a first filter. The volume of the first filter was 1.78 milliliters, The two fiber-packed columns were connected as shown in FIG. 9.

The outlet nipple of a 25 milliliter injector was inserted into the conduit 7' of the first filter 5'. 5 milliliters of heparinized blood from a healthy human donor were heated to a temperature of 37° C., and then, by means of the injector, sucked into the conduit 4' of the second filter 1' and flowed through the second filter 1' and the first filter 5' at a flow rate of 3 milliliters/minute. When the movement of the blood from the second filter 1' to the first filter 5' stopped, the suction caused by the injector was also stopped, and the two filters 1' and 5' were disconnected from each other. Then, 20 milliliters of a physiological sodium chloride solution were sucked into the conduit 11' of the first filter 5' by means of the injector and flowed through the first filter 5' at a flow rate of 5 milliliters per minute. Then, the injector was detached from the conduit 7', and thereafter another injector filled with 2 milliliters of a physiological sodium chloride solution was fitted to the conduit 7'. The physiological sodium chloride solution was abruptly forced into the first filter 5' thereby to collect 2 milliliters of a lymphocyte-rich suspension from the conduit 11'. The concentration of the collected lymphocytes in the suspension was 70% of the original lymphocyte concentration in the blood. The collected lymphocytes exhibited a viability of at least 99%. The total amount of granulocytes and monocytes contained in the collected lymphocyte-rich suspension was 7% of the total amount of all leukocyte components, that is, the amount of lymphocytes contained in the collected suspension was 93% of the total amount of all leukocyte components (i.e. the purity of lymphocytes was 93%). The collected lymphocyte-rich suspension further contained 0.8% of the original etythrocytes and 4% of the original platelets.

EXAMPLE 3

1.448 grams of polyester fibers having an average diameter of 14.3 microns and a length of about 50 millimeters were uniformly packed at a bulk density of 0.18 gram/cubic centimeter into a cylindrical polystyrene column having an inner diameter of 16 millimeters and a length of 40 millimeters, thereby to prepare a second filter. 0.471 gram of polyamide fibers having an average diameter of 10.6 microns and a length of about 30 millimeters was uniformly packed at a bulk density of 0.20 gram/cubic centimeter into a cylindrical polystyrene column having an inner diameter of 10 millimeters and a length of 30 millimeters, thereby to prepare a first filter. The two filters so prepared were disposed as shown in FIG. 3.

The outlet nipple of a 25-milliliter injector was inserted into the conduit 7 of the first filter 5. 9 milliliters of heparinized blood from a healthy human donor were heated to a temperature of 37° C., and then, by means of the injector, sucked through the conduit 4 of the second filter 1 and into the second filter 1 and the first filter 5 at a flow rate of about 2 milliliters/minute. When the second and first filters were filled with the blood, the suction caused by the injector was stopped. Then, 2 milliliters of serum of the AB type were similarly sucked into the two filters at a flow rate of 2 milliliters/minute. Thereafter, the injector was detached from the conduit 7 and fitted to the conduit 4, and then 30 milliliters of a physiological sodium chloride solution were sucked through the conduit 7 into the two filters and flowed therethrough at a flow rate of 4 milliliters/minute. Then, the injector was detached from the conduit 4, and, in place of the injector, another injector filled with 2 milliliters of a physiological sodium chloride solution was fitted to the conduit 4. The physiological sodium chloride solution was abruptly forced into the two filters 1 and 5 thereby to collect 2 milliliters of a lymphocyte-rich suspension from the conduit 7. The concentration of the collected lymphocytes in the suspension was 60% of the original lymphocyte concentration in the blood. The total amount of granulocytes and monocytes contained in the collected suspension was 8% of the total amount of all leukocyte components, that is, the amount of lymphocytes contained in the collected suspension was 92% of the total amount of all leukocyte components (i.e., the purity of the collected lymphocytes was 92%). The collected suspension further contained 1.4% of the original erythrocytes and 5% of the original platelets.

EXAMPLE 4

0.198 gram of polyester fibers having an average diameter of 12.4 microns and a length of about 3.8 centimeters was uniformly packed at a bulk density of 0.12 gram/cubic centimeter into a cylindrical polystyrene column having an inner diameter of 14.5 millimeters and a length of 10 centimeters, thereby to prepare a second filter. The volume of the second filter was 1.5 milliliters. 0.294 gram of polyester fibers having an average diameter of 9 microns and a length of about 40 millimeters was uniformly packed at a bulk density of 0.16 gram/cubic centimeter into another cylindrical polystyrene column having an inner diameter of 12.5 millimeters and a length of 15 millimeters, thereby to prepare a first filter. The volume of the first filter was 1.63 milliliters. The two fiber-packed columns were connected as shown in FIG. 9.

The outlet nipple of a 25 milliliter injector was inserted into the conduit 7' of the first filter 5' and an injector needle was connected to the conduit 4' of the second filter 1'. About 3.2 milliliters of blood were extracted from the vein of a healthy human donor through the injector needle at a flow rate of about 2 milliliters/minute. Then, the two filters 1' and 5' were separated from each other. 20 milliliters of a physiological sodium chloride solution were then sucked through the conduit 11' into the first filter 5' at a flow rate of about 5 milliliters/minute. Then, the injector was detached from the conduit 7', and, in place of the injector, another injector filled with 2 milliliters of a physiological sodium chloride solution was fitted to the conduit 7'. The physiological sodium chloride solution was abruptly forced into the first filter 5' thereby to collect 2 milliliters of a lymphocyte-rich suspension from the conduit 11'. One milliliter of heparinized blood was extracted from the same donor, and a comparison test of this blood with the collected lymphocyte-rich suspension was conducted. The comparison test showed that the concentration of the collected lymphocytes in the suspension was 60% of the original lymphocyte concentration in the blood. The purity of the collected lymphocytes was 95%. The collected suspension further contained 0.6% of the original erythrocytes and 3% of the original platelets. Although no anit-coagulant was used in this experiment, the collected lymphocyte-rich suspension did not coagulate. This fact clearly indicates that anti coagulants normally used in separating lymphocytes need not be used for separating lymphocytes according to the present invention. Thus, the lymphocytes collected by utilizing the process of the present invention will not be subjected to the deleterious effects of anticoagulants.

What we claim is:

1. An apparatus for separating lymphocytes from blood or other lymphocyte-containing suspensions, comprising:
    a first filter comprising a container having an inlet and an outlet, said container having packed therein a mass of fibers exhibiting a bulk density of from 0.04 to 0.40 gram/cubic centimeter and an average fiber diameter of from 5 to 20 microns, and
    a second filter, disposed upstream to or downstream from said first filter, comprising a container having an inlet and an outlet, said container having packed therein a mass of fibers exhibiting an average fiber diameter of greater than 10 microns but not greater than 60 microns, the average fiber diameter of said second filter being greater than that of said first filter,
    said outlet of one of said two filters being connected to said inlet of said other filter.

2. An apparatus according to claim 1 wherein a conduit of said outlet of one of said two filters and a conduit of said inlet of said other filter are connected to at least one other conduit.

3. An apparatus according to claim 1 wherein a conduit of said outlet of one of said two filters can be disconnected from a conduit of said inlet of said other filter.

4. An apparatus according to claim 1 wherein said container of said first filter has packed therein a mass of fibers exhibiting a bulk density of from 0.04 to 0.25 gram/cubic centimeter and an average fiber diameter of from 7 to 10 microns.

5. An apparatus according to claim 1 wherein said fibers are of at least one type of fibers selected from the group consisting of synthetic fibers, semi-synthetic fibers, regenerated fibers, natural fibers and inorganic fibers.

6. An apparatus according to claim 1 wherein the volume of the first filter is 0.2 to 5 milliliters and the volume of the second filter is 0.5 to 5 milliliters.

7. An apparatus according to claim 2 wherein at least one outlet conduit of said two containers is of a form capable of being connected to the outlet nipple of an injector.

8. An apparatus according to claim 2 wherein at least one inlet conduit of said two containers is of a form capable of being connected to the outlet nipple of an injector.

9. An apparatus according to claim 2 wherein at least one inlet conduit of said two containers is of a form capable of being connected to an injector needle or said inlet conduit comprises an injector needle.

10. An apparatus according to claim 2 wherein said inlet conduit of one of said two filters, which is disposed upstream to the other of said two filters, is capped with a rubber covering to be pierced by an injector needle.

11. A method of separating lymphocytes from a lymphocyte-containing suspension comprising the steps of:
    causing said lymphocyte-containing suspension to flow through a second filter comprising a container having packed therein a mass of fibers exhibiting an average fiber diameter of greater than 10 microns but not greater than 60 microns, thereby to entrap a substantial part of granulocytes and monocytes in said mass of fibers and to obtain a granulocyte-poor and monocyte-poor lymphocyte-containing suspension,
    causing said granulocyte-poor and monocyte-poor lymphocyte-containing suspension to flow through a first filter comprising a container having packed therein a mass of fibers exhibiting a bulk density of from 0.04 to 0.40 gram/cubic centimeter and an average fiber diameter of from 5 to 20 microns, said average fiber diameter being less than that of said second filter, thereby to entrap a substantial part of lymphocytes in said means of fibers, and then
    collecting said lymphocytes entrapped in said mass of fibers of said first filter, to obtain a lymphocyte-rich suspension.

12. A method of separating lymphocytes from a lymphocyte-containing suspension comprising the steps of:
    causing said lymphocyte-containing suspension to flow through a first filter comprising a container having packed therein a mass of fibers exhibiting a bulk density of from 0.04 to 0.40 gram/cubic centimeter and an average fiber diameter of from 5 to 20 microns, thereby to entrap a substantial part of leukocyte components in said mass of fibers,
    collecting said leukocyte components entrapped in said mass of fibers of said first filter, to obtain a leukocyte component-rich suspension, and then
    causing said leukocyte component-rich suspension to flow through a second filter comprising a container having packed therein a mass of fibers exhibiting an average fiber diameter of greater than 10 microns but not greater than 60 microns, the average fiber diameter of said second filter being greater than that of said first filter, thereby to entrap a substantial part of granulocytes and monocytes in said mass of fibers of said second filter and to obtain a lymphocyte-rich suspension.

* * * * *